United States Patent [19]

Storrs

[11] 4,226,940
[45] Oct. 7, 1980

[54] NON-FROZEN CONCENTRATED BACTERIAL CULTURES

[75] Inventor: Arnold B. Storrs, Solon Mills, Ill.

[73] Assignee: Great Lakes Biochemical Co., Inc., Milwaukee, Wis.

[21] Appl. No.: 50,886

[22] Filed: Jun. 21, 1979

Related U.S. Application Data

[63] Continuation-in-part of Ser. No. 871,231, Jan. 23, 1978, abandoned.

[51] Int. Cl.$^3$ ............................................. C12N 1/04
[52] U.S. Cl. .................................... 435/260; 435/822; 435/853; 435/854; 435/855; 435/856; 435/857; 435/885
[58] Field of Search ............... 435/260, 253, 853, 854, 435/855, 856, 857, 885, 822

[56] References Cited

U.S. PATENT DOCUMENTS

| | | | |
|---|---|---|---|
| Re. 28,276 | 12/1974 | Farr | 435/260 |
| Re. 28,488 | 7/1975 | Farr | 435/260 X |
| 3,975,545 | 8/1976 | Vedamuthu | 435/260 X |

Primary Examiner—Robert J. Warden
Attorney, Agent, or Firm—Michael, Best & Friedrich

[57] ABSTRACT

A concentrated bacterial culture, capable of being cooled to temperatures as low as about −40° C. for storage without rapid freezing and with minimum damage to the bacterial cells, is prepared by diluting a conventionally prepared concentrated cell paste with a liquid anti-freeze agent containing one or more water freezing point depressants which are water-soluble, are non-injurious to the bacteria, and do not form crystals when cooled to a predetermined temperature within the range of about 5 to about −40° C. The amount of the freezing point depressant(s) is sufficient to prevent formation of ice crystals from the water present in the diluted product when cooled to the predetermined temperature. The culture, which does not become hard or crystalline upon being cooled to temperatures as low as −40° C., can be warmed to a temperature convenient for sampling, assaying and blending and then re-cooled to a cold storage temperature without an appreciable reduction in viability.

17 Claims, No Drawings

NON-FROZEN CONCENTRATED BACTERIAL CULTURES

CROSS REFERENCE TO RELATED APPLICATION

This application is a continuation-in-part of application Ser. No. 871,231, filed Jan. 23, 1978 now abandoned, which is incorporated herein by reference.

BACKGROUND OF THE INVENTION

This invention relates to concentrated bacterial cultures and, more particularly, to a process for preparing concentrated bacterial culture products which are stored at very low temperatures for the preservation of viability.

Bacterial cultures having closely controlled activites have been developed for use in initiating fermentation in a variety of processes, including those for production of various fermented dairy products, such as cheese, buttermilk, yogurt, etc., and the production of other foods, such as sausage, pickles and sauerkraut, as well as animal feeds such as silage and bacterial concentrates for direct use as nutritional supplements. Fermentation cultures generally fall into three categories: (1) normal fermented cultures for immediate use or transfer, (2) frozen cultures, either at normal strength or concentrated, and (3) dried cultures, principally freeze-dried.

In recent years, the use of frozen, highly concentrated cultures, prepared by rapid freezing and stored in the frozen state until immediately prior to use, has become more widespread because viability of the bacteria can be maintained for extended periods of time. However, such cultures are not without certain shortcomings. Frozen bacterial concentrates typically are prepared by inoculating a selected strain or strains of bacterial cells into a suitable growth medium, incubating the medium under suitable temperature and pH conditions until the desired yield of bacterial cells is reached, and then harvesting these cells by concentrating the medium with a centrifuge. The resulting cell paste containing some water is diluted with a water-soluble diluent to a consistency convenient for packaging and the diluted culture product, which is a water-based suspension of cells, is frozen to preserve the viability of the cells.

This freezing process can cause damage to the cells if there is a formation of ice crystals which can puncture or otherwise physically damage the cell walls. This potential problem can be minimized by rapidly freezing the diluted cell paste in a liquid nitrogen or dry ice bath. This rapid freezing promotes the formation of small ice crystals which generally do not cause as much damage as larger ice crystals typically formed during slower freezing.

In addition to the added costs associated with such rapid freezing processes, the abrupt change in the physical state of the cells can have an adverse effect on the subsequent cell activity. After being frozen, the culture must be stored in a frozen state, preferably at a temperature of at least $-30°$ C. or lower, until just prior to use when it must be thawed with care. Generally, the frozen culture cannot be thawed and then re-frozen prior to use because re-freezing, or even a cycling of storage temperatures between the freezing point and about $-30°$ C., can cause a formation of damaging ice crystals. Consequently, the culture, after being frozen, cannot be conveniently sampled to assay activity or thawed to withdraw a portion for blending with another culture and then re-frozen.

Also, frozen cultures usually require the use of dry ice for transportation in order to maintain the temperature below a level where a significant loss of viability occurs. Because of the additional precautions required in handling and maintaining dry ice-cooled shipping containers, commercial carriers often charge a premium for transporting same. Some commercial carriers, particularly commercial airlines, refuse to accept dry ice-cooled shipping containers for shipment because of the carbon dioxide gas venting therefrom.

U.S. Pat. No. Re. 28,276 describes the use of 2-25% of glycerol and U.S. Pat. No. 3,975,545 describes the use of alkali metal salts of glycerophosphoric acid, either alone or in combination with glycerol, as stabilizing agents for reducing cell damage during freezing. However, in both instances, the culture is still frozen to a hard or crystalline state for storage with the attendant processing, handling and transportation problems, and the stabilizing agent is used at concentrations intended to minimize cell damage through the trauma of the freezing process.

A principal object of the invention is to provide a process for preparing non-frozen concentrated bacterial cultures which can be slowly cooled, if desired, to cold storage temperatures necessary for preserving viability with minimal damage to the bacterial cells.

Another object of the invention is to provide non-frozen concentrated bacterial cultures which can be repeatedly cooled to a storage temperature as low as about $-40°$ C. and warmed to a temperature convenient for sampling, assaying and the like without a significant reduction in viability.

A further object of the invention is to provide an efficient method for preparing mixed strains of concentrated bacterial cultures from cultures which have been stored for some time.

A still further object of the invention is to provide an anti-freeze agent for diluting concentrated bacterial pastes and inhibiting the formation of damaging ice crystals when the diluted paste is subsequently cooled to sub-freezing storage temperatures.

Other objects, aspects and advantages of the invention will become apparent to those skilled in the art upon reviewing the following detailed description and the appended claims.

The invention provides a liquid anti-freeze agent which is admixed with a concentrated bacterial paste prepared in a conventional manner and inhibits the formation of damaging ice cells when the diluted paste is subsequently cooled to temperatures as low as about $-40°$ C. for preserving the viability of the bacterial cells. The anti-freeze agent contains one or more water freezing depressants which are water-soluble, are non-injurious to the particular bacteria, and do not form crystals when cooled to a predetermined temperature within the range of about 5° to about $-40°$ C. The amount of anti-freeze agent added to the concentrated bacterial paste is sufficient to prevent freezing of the water present in the resultant mixture when it is subsequently cooled to the predetermined temperature. The resultant non-frozen culture can be repeatedly cycled between a storage temperature and temperatures above 5° C. without a significant loss of viability.

DESCRIPTION OF THE PREFERRED EMBODIMENTS

Generally, the invention is applicable to any bacterial culture which can be concentrated and cooled to a temperature of about −40° C. to preserve viability. The preferred bacteria fall within Division I of Class II, Order 4, Eubacteriales, *Bergey's Manual of Determinative Bacteriology*. Representative suitable bacteria include *Streptococcus cremoris, Streptococcus diacetilactis, Streptococcus citrovorous, Streptococcus lactis, Streptococcus paracitrovorus, Streptococcus thermophilus, Streptococcus faecalis, Streptococcus durans, Lactobacillus acidophilus, Lactobacillus bulgaricus, Lactobacillus brevis, Lactobacillus delbrueckii, Lactobacillus fermenti, Lactobacillus helveticus, Lactobacillus lactis, Lactobacillus plantarum, Lactobacillus thermophilus, Lactobacillus casei, Leuconostoc citrovorum, Leuconostoc mesenteroides,* propionibacterium species, and mixtures thereof.

As mentioned above, a concentrated paste of the bacterial cells is prepared in a conventional manner. For instance, a selected bacterial culture is inoculated into a suitable nutrient medium, the inoculated medium incubated under suitable temperature and pH conditions to obtain a desired yield of bacterial cells, and the cells are harvested as a paste. Various known culture media can be employed including milk-based substrates, such as whole milk, skim milk, cream, etc. The length of time required to provide an adequate growth of bacterial cells depends upon the particular type and growth characteristics of the strain of bacteria employed, the size of the inoculum, the culture medium employed, the temperature of incubation, etc.

As a guide, a suitable culture can be prepared by inoculating a *S. diacetilactis* culture into an aqueous nutrient medium containing 1 wt. % dried skim milk, 0.5 wt. % sodium citrate, 1.5 wt. % dextrose, 1 wt. % yeast extract, 0.05 wt. % magnesium sulfate, 0.004 wt. % sodium sulfite, and 0.0067 wt. % manganese chloride as the active ingredients. The inoculated medium is incubated at 25°-30° C. with the pH thereof being adjusted and maintained at about 5.5-6 by adding a controlled amount of an alkali as required until cell growth is completed. At the termination of incubation, the medium is cooled to a temperature of about 15° to about 20° C. and viable cells are then harvested from the cooled medium as a concentrated paste containing about 30 wt. % solids by collecting with a supercentrifuge. The concentrated bacterial paste is diluted with a liquid anti-freeze agent of the invention and the thus-diluted bacterial culture is cooled to a temperature at which the metabolism thereof is reduced to a very low level or a dormant state. The resultant culture, which has a consistency ranging from a heavy, syrupy liquid to viscous plasticity, instead of the typical hard crystalline body of conventional frozen cultures, can be stored at temperatures down to about −40° C. until ready for use.

The liquid anti-freeze agent provided by the invention serves as a vehicle for diluting the concentrated bacterial paste to a consistency convenient for handling and packaging. It includes one or more water freezing point depressants which combine with the water present in the resultant mixture and depresses the freezing point thereof to a level where the diluted paste can be slowly cooled to a predetermined temperature within the range of about 5 to about −40° C. without formation of any appreciable amount of ice crystals or other crystalline structures.

Various suitable water freezing point depressants can be used as long as they: (1) are water-soluble, (2) are compatible with or non-injurious to the bacteria in the culture, and (3) do not form crystals when cooled to a predetermined temperature within the range of about 5° to about −40° C.

Suitable water freezing point depressants include polyhydric alcohols, such as glycerol, propylene glycol, polyethylene glycol, sorbitol and mannitol; sugars, such as invert sugar, fructose, corn syrup, high fructose corn syrup hydrolyzed corn syrup, dextrose, sucrose, maltose, lactose, and other carbohydrates containing levulose; and other water-soluble inorganic and organic compounds heretofore used as cryoprotective agents in frozen bacterial concentrates, particularly organic salts such as glutamates (e.g., monosodium glutamate), gluconates, cyclomates, and the like. Of the above-mentioned sugars, invert sugar, fructose and high fructose corn syrup presently are preferred because they are readily soluble in water at room and lower temperatures and do not tend to form crystals readily when cooled to temperatures as low as about −40° C. High fructose corn syrup is particularly preferred because of its low molecular weight, high water solubility, high hygroscopicity and tendency not to crystallize easily. Also, it is edible and nutritious and, therefore, is highly acceptable for use in food products. Dextrose, another common monosaccharide, has substantially the same molecular weight as fructose and has about the same physical effect as fructose in depressing the freezing point. However, dextrose tends to crystallize more readily and is less soluble and, consequently, is somewhat less desirable.

Cornsweet 90, marketed by Archer-Daniels-Midland Co., is an example of a commercially available high fructose corn syrup which is particularly suitable as a freezing point depressant. Approximately 90% of the sugar solids of this product is fructose as compared to invert sugar which commonly contains about 50% of the total sugar solids as fructose.

While some of the freezing point depressants can be used alone, a mixture of two or more from the different classes mentioned above has been found to be more effective. When a suitable liquid polyhydric alcohol, such as glycerol, is used, it can serve both as one of the freezing point depressants and the diluent for the other freezing point depressant(s). Some of the freezing point depressants can serve as the anti-freeze agent by itself. However, others, particularly glycerol, cannot be used by themselves because of a tendency to become toxic at concentrations required to prevent freezing at temperatures as low as −40° C. If desired, the anti-freeze agent can include water or another suitable solvent or diluent which does not serve as a freezing point depressant so long as the resultant mixture meets the three criteria mentioned above. Generally, when water is included as one of the ingredients of the anti-freeze agent, the amount thereof should be less than about 20 wt. %, based on the total weight of the anti-freeze agent.

If high fructose corn syrup is the sole freezing point depressant, the amount used usually is about 45 to about 75 weight % of the total weight of water and corn syrup in the finished culture product. If invert sugar is the sole freezing point depressant, the amount used usually is about 60 to 90 weight % of the total weight of water and invert sugar in the finished culture product.

Some of the anti-freezing point depressants mentioned above, such as glycerol, have been employed heretofore as bacterial culture diluents and/or stabilizing agents. However, to the best of applicant's knowledge, they have not been used in sufficient concentrations to prevent the bacterial culture from becoming hard or crystalline upon being cooled to subfreezing storage temperatures as required by the present invention.

The effectiveness of the freezing point depressant(s) in the anti-freeze agent to lower the freezing point of water in the diluted concentrated bacterial culture, and thus inhibit the formation of damaging ice crystals, is a function of the molar concentration of the freezing point depressant(s) in solution. Inasmuch as the molecular weight of the various freezing point depressants suitable for use in the anti-freeze agent vary over a relatively broad range, it is not feasible to define a precise range which will encompass the effective amounts of the freezing point depressants. Also, the amount of freezing point depressant(s) added to the concentrated bacterial paste depends upon the temperature to which the diluted paste is to be cooled for storage and handling. For example, a storage temperature of about $-18°$ C. may be adequate for retaining the viability of one bacterial culture while another may require a temperature as low as about $-35°$ C. Another factor affecting the amount of freezing point depressant(s) added with the anti-freeze agent is the amount of water in the anti-freeze agent, if any, and the amount of water present in the concentrated bacterial paste prior to dilution.

Consequently, it is usually necessary to determine acceptable formulations of the anti-freeze agent for a particular bacterial culture by routine trial and error testing. That is, a number of anti-freeze agents having different amounts of the freezing point depressant(s) are made up and admixed with samples of the concentrated bacterial paste, the diluted samples of bacterial paste cooled to the minimum temperature they might be expected to encounter during handling and storage, and the cooled samples examined for the presence of ice crystals. The presence of any appreciable amount of ice crystals is considered unacceptable.

Potentially acceptable formulations for the anti-freeze agent can be determined by calculating the chemical activity of the total water present in the diluted bacterial culture. The chemical activity of the water ($A_w$) can be approximated by Raoult's Law which can be expressed as follows:

$$A_w = \frac{\text{moles of total water}}{\text{moles of total water + moles of freezing point depressant(s)}}$$

It has been found that anti-freeze agents including freezing point depressants meeting the above-mentioned criteria and providing a calculated water activity of less than about 0.95, preferably less than about 0.9, are generally effective in preventing the formation of damaging ice crystals when the diluted culture is cooled to a temperature as low as about $-40°$ C. However, this calculated value for water activity should be used as a guide for formulating the anti-freeze agent. Samples of diluted bacterial paste still should be tested by the trial and error procedure described above in order to insure that the anti-freeze agent provides the desired protection against the formation of damaging ice crystals when the diluted bacterial culture is cooled to the desired cold storage temperature. As further guides, the concentration of the freezing point depressant(s) in the diluted bacterial culture generally should be at least 40 weight %, based on the total weight of the diluted culture, and the concentration of the freezing point depressant(s) in the anti-freeze agent generally should be at least 50 weight %, based on the total weight of the anti-freeze agent.

Two particularly suitable anti-freeze agents for a variety of bacteria, including the specific ones mentioned above, have the following formulations:

| Formulation A | |
|---|---|
| Ingredient | Weight % |
| Glycerol | 40 |
| Invert sugar | 40 |
| Monosodium glutamate | 10 |
| Water | 10 |
| | 100 |

| Formulation B | |
|---|---|
| Ingredient | Weight % |
| High fructose corn syrup | 80 |
| Glycerol | 10 |
| Monosodium glutamate | 5 |
| Water | 5 |
| | 100 |

A concentrated bacterial culture prepared from a concentrated paste having a solids content of about 30 weight % and diluted with approximately two parts of the above anti-freeze agents usually will have a water activity value of about 0.8.

The anti-freeze agent is thoroughly admixed with the concentrated bacterial paste and the diluted paste is introduced into storage containers or packages which can be placed in a conventional freezer set at a predetermined temperature within the range of about 5° C. (40° F.) to about $-40°$ C. ($-40°$ F.) for cooling and storage. Since there is no appreciable freezing or formation of ice crystals, there is no need for ultra-fast freezing heretofore required to prevent the formation of large ice crystals. Instead, the cooling can proceed at a rate normally provided by conventional freezing equipment, thereby eliminating the need for more expensive rapid freezing equipment. As mentioned above the resultant culture does not become hard or crystalline and, instead, has a consistency ranging from a heavy, syrupy liquid to viscous plasticity, depending on the temperature and the specific amount and type of anti-freeze agent used.

Storing bacterial cultures at a temperature within the range of so-called frozen storage is an effective and simple means for preserving viability and activity for extended periods of time. The formation of ice crystals during cooling to a cold storage temperature usually is the cause of bacterial cell destruction in prior art processes rather than the cold temperature itself. The invention, by minimizing the formation of ice crystals, eliminates or minimizes one of the shortcomings of prior art processes for producing frozen bacterial concentrates and provides a new category of fermentation cultures in addition to the three categories mentioned above, namely, a concentrated bacterial culture which can be stored at a temperature within the frozen storage range to preserve viability and activity without becoming hard or crystalline. This new category can be referred to as "non-frozen concentrated bacterial cultures."

The concentrated culture usually is stored at a frozen storage temperature, e.g., about −30° to about −35° C., until ready for use because the viability and activity can be effectively maintained in this manner. However, the culture is substantially less heat sensitive than prior art frozen bacterial concentrates. It can be stored at temperatures approaching 0° C. for several days without an appreciable loss in viability. Thus, it can be transported in conventional picnic type coolers employing so-called frozen "blue ice" bags commonly used with such coolers instead of dry ice-cooled containers required for conventional frozen cultures.

The concentrated culture can be removed from cold storage, allowed to warm up to a temperature (e.g., about 5° C.) where it can be readily blended with another culture or a sample taken and then returned to cold storage with negligible loss of viability. This capability makes it possible to sample the culture concentrate whenever desired to assay its activity or to remove a portion for use such as in the production of different culture blends, none of which activities are practical with prior art frozen bacterial concentrates.

This capability of withstanding temperature cycling permits the establishment of what can be called "culture banks" for storing or banking a variety of single strain cultures. That is, single strains of concentrated cultures can be prepared separately, diluted with an anti-freeze agent as described above and cold stored in separate bulk containers. When it is desired to produce a particular blended culture, selected single strains can be removed from cold storage, allowed to warm to a temperature suitable for mixing, and appropriate quantities of each removed from the bulk container and mixed together to obtain the desired blend. The mixed culture can be used or packaged in the normal manner and placed in cold storage for future use. The bulk single strain cultures likewise can be returned to the cold storage "bank" until needed again. Thus, a large variety of culture blends can be made available for immediate use from such a "culture bank", with a readily apparent simplification in maintaining a ready inventory of cultures.

It has been found that, in many cases, non-frozen concentrates of the invention exhibit higher cell counts than frozen concentrates, particularly when a high fructose containing anti-freeze agent is used.

Without further elaboration, it is believed that one skilled in the art can, using the preceding description, utilize the present invention to its fullest extent. The following examples are presented to illustrate the invention and are not to be construed as limitations thereof.

EXAMPLE I

Three strains of S. cremoris were inoculated into a nutrient medium and incubated for 14 to 16 hours at a temperature of about 24° C. The pH of the medium was maintained at a level above 5.5 by an electronic controller which automatically introduced appropriate amounts of a sodium hydroxide solution into the medium. At the termination of incubation, the medium was cooled to about 15° C. and then transferred to a supercentrifuge which was operated at about 12,000 g's. 50 gm of the resultant concentrated bacterial paste were mixed with 7.5 gm of a liquid concentrate of L. citrovorum and 92.5 gm of an anti-freeze agent having Formulation A above. 0.5 Ounce samples of the resultant mixture were placed in separate small bottles and stored in a conventional freezer set at −35° C. wherein the samples were cooled without the use of rapid freezing normally used for prior art frozen bacterial concentrates. The resultant concentrate had a heavy syrupy consistency.

Another portion of the culture was assayed for activity at the time of production by inoculating 32 ppm into a 9% solids, non-fat milk and incubating same at 22° C. for 16 hours. At the end of the test period, the pH of the milk was reduced to 4.5 and the titratable acidity was 0.80%, which is indicative of good performance at the levels recommended for the production of buttermilk or cottage cheese. Similar activity tests were performed on one of the samples in cold storage at three different time intervals after production. For each test, the sample bottle was removed, warmed briefly from −35° C. to 0°–5° C., a portion of the culture withdrawn for testing, and the bottle containing the balance of the culture returned to the freezer and stored at −35° C. until the next test period. The activities for each test were as follows:

| Time Interval After Initial Cooling at 35° C. | pH | Activity Titratable Acidity, % |
|---|---|---|
| 3 weeks | 4.50 | 0.79 |
| 5½ months | 4.42 | 0.93 |
| 7½ months | 4.55 | 0.86 |

From these test results, it can be seen that there was no significant reduction in the activity of the culture after 7½ months of cold storage even though it was subjected to three temperature cycles between −35° C. and 0°–5° C. and was not rapidly cooled.

EXAMPLE 2

A blended culture for use in the production of buttermilk was prepared by mixing two different strains of S. cremoris with L. citrovorum. Each individual strain was grown separately and harvested as a concentrated bacterial paste in a conventional manner. Each paste was diluted with two parts of an anti-freeze agent of Formulation A above as in Example 1 and stored in a conventional freezer at −35° C. until needed. Individual cultures were removed from cold storage, warmed to about 0°–5° C. and appropriate portions combined to produce the desired buttermilk culture. The age and amounts of the individual strains used were as follows:

| Individual Strain | Age at Time of Mixing, days | Amount, kg. |
|---|---|---|
| S. cremoris | 6 | 7.625 |
| S. cremoris | 31 | 7.625 |
| L. citrovorum | 5 | 0.850 |

The S. cremoris strains were the primary organisms in the mixture for producing lactic acid. Each of the S. cremoris concentrates were assayed after production and prior to cooling to determine its activity in the same manner described above. The pH of the milk was reduced to 4.61 and 4.79 by the respective strains which means that a combination of these two strains in equal amounts would be expected to reduce the pH of the milk to approximately 4.70. The mixed culture was assayed in the same manner to determine its activity.

The milk was reduced to a pH of 4.69 and had a titratable acidity of 0.82%, indicating there was no appreciable loss in the activities of the individual *S. cremoris* strains even though they had been stored for different time periods and blended together after storage at a temperature of −35° C.

EXAMPLE 3

Individual strains of *L. lactis*, *L. plantarum*, *S. cremoris* and *S. diacetilactis* were grown separately and harvested as a concentrated bacterial paste at different times. Each paste was diluted with two parts of an anti-freeze agent having Formulation A above and stored at −35° C. for future use in a conventional freezer serving as a "culture bank". While in storage, a portion of each culture was withdrawn, after the culture had been warmed to facilitate sampling, and assayed for viability by a total plate count of organisms. Based on the measured viability of each strain, a culture for fermenting silage having the formulation below was prepared. The actual plate count per gram of the resultant silage culture was measured and compared with the calculated plate count.

| Organism | Amount kg | Count Per Gram, $\times 10^9$ | Total Organisms, $\times 10^{12}$ |
|---|---|---|---|
| L. lactis | 69.8 | 69.0 | 4816 |
| L. lactis | 25.0 | 86.5 | 2163 |
| L. plantarum | 53.7 | 110.0 | 5907 |
| S. cremoris | 9.0 | 146.0 | 1314 |
| S. diacetilactis | 9.0 | 98.0 | 882 |
| Anti-freeze agent | 33.5 | — | — |
| Total | 200 | | 15082 |

Calculated plate count per gram = $75.4 \times 10^9$
Actual plate count per gram = $79.5 \times 10^9$ The silage culture was prepared by removing the individual strains of culture from the "culture bank", warming them to about 0°–5° C. to facilitate mixing, combining each in the above proportion and packaging 250 gm aliquots of the resultant silage culture in separate sealed cans. The cans containing the silage culture were returned to the "culture bank" and stored at −35° C. The silage culture was subsequently used to successfully produce silage.

EXAMPLE 4

Separate portions of a concentrated cell paste of *L. acidophilus* from the same batch were used to prepare liquid concentrates. One liquid concentrate (A) was prepared by mixing 1 part of the cell paste with 2.5 parts of a conventional phosphate-citrate buffer diluent used in the production of frozen bacterial concentrates. The resultant diluted concentrate was placed in sealed aluminum cans, rapidly frozen in an acetone-dry ice bath and stored at −35° C. The other liquid concentrate (B) was prepared by admixing 1 part of the cell paste with 2 parts of an anti-freeze agent having the same composition as in Example 1. The resultant diluted concentrate was placed in a closed bulk container and stored at −35° C. without prior freezing. Measured plate counts of the two concentrates, taken at the time of production and after two months storage, were as follows:

| Concentrate | Plate Counts Initial | After 2 Months |
|---|---|---|
| A | $79 \times 10^9$ | $70 \times 10^9$ |
| B | $130 \times 10^9$ | $103 \times 10^9$ |

From these test results, it can be seen that the degree of viability and stability of the concentrate (B) prepared in accordance with the invention was comparable to that of a frozen concentrate (A) prepared in a conventional manner.

EXAMPLE 5

Individual strains of *L. brevis*, *L. plantarum*, *S. cremoris* and *S. diacetilactis* were grown separately and harvested as a concentrated bacterial paste at different times. Each paste was diluted at the same ratio with an anti-freeze agent having Formulation B above (using Cornsweet 90 as high fructose corn syrup) and stored at −35° C. for future use in a conventional freezer serving as a "culture bank". Each culture was assayed for viability prior to initial storage. After storage for some time, a portion of each culture was withdrawn in the manner described in Example 3 and a concentrated culture for silage fermentation having the formulation below was prepared. The actual plate count per gram of the resultant silage culture was measured and compared with the calculated plate count.

| Organism | Amount kg | Count Per Gram at Initial Storage $\times 10^9$ | Calculated Total Organisms, $\times 10^{12}$ | Age at Time of Blending, Days |
|---|---|---|---|---|
| L. brevis | 14.15 | 196 | 2773 | 43 |
| L. brevis | 22.00 | 119 | 2618 | 12 |
| L. plantarum | 22.00 | 257 | 5654 | 20 |
| S. cremoris | 6.00 | 229 | 1374 | 13 |
| S. diacetilactis | 7.15 | 87 | 622 | 6 |
| Anti-freeze agent | 165.00 | — | — | |
| Water | 19.00 | — | — | |
| Total - | 255.30 | | 13041 | |

Calculated plate count per gram = $51.08 \times 10^9$
Actual plate count per gram = $51.0 \times 10^9$ From these results, it can be seen that all the culture strains retained their activity even though stored for different time periods at 35° C.

EXAMPLE 6

Both frozen and non-frozen concentrates of *S. diacetilactis* were produced at the same concentration for commercial use. The frozen concentrates were prepared by mixing 1 part of cell paste with 3.25 parts of a conventional phosphate buffer. The non-frozen concentrates were prepared by mixing 1 part of cell paste with 3.25 parts of a liquid anti-freeze agent of Formulation B above. Over a five month period of production, batches of the two concentrates had the following cell counts:

| | Plate Count, $\times 10^9$/gm. |
|---|---|
| Frozen Concentrates | 123 |

| | Plate Count, × 10⁹/gm. |
|---|---|
| | 217 |
| | 110 |
| | Average = 150 |
| Non-Frozen Concentrates | 179 |
| | 142 |
| | 225 |
| | 264 |
| | 175 |
| | Average = 197 |

These results indicate the use of an anti-freeze agent in accordance with the invention is more efficient than a conventional frozen concentrate in view of the fact that a higher number of cells survived in the finished product.

From the foregoing description, one skilled in the art can easily ascertain the essential characteristics of the invention and, without departing from the spirit and scope thereof, can make various changes and modifications to adapt the invention to various usages and conditions.

I claim:

1. In a process for preparing a concentrated bacterial culture which can be cooled to a subfreezing temperature for preserving the viability of the bacteria for an extended time including the steps of inoculating an aqueous bacterial nutrient medium with a culture of the bacteria, incubating the inoculated medium under suitable conditions to obtain a desired yield of bacterial cells, and concentrating the medium to obtain a concentrated bacterial paste containing water, the improvement comprising admixing with said paste a liquid anti-freeze agent containing at least one water freezing point depressant which is water-soluble, is non-injurious to the bacteria, and does not form crystals when cooled to a predetermined temperature within the range of about 5° to about −40° C., the amount of said water freezing depressant in said anti-freeze agent being sufficient to prevent formation of ice crystals from the water present in the resultant mixture when the resultant mixture is cooled to said predetermined temperature.

2. A process according to claim 1 wherein the bacteria selected is an organism falling within the classification Eubacteriales.

3. A process according to claim 2 wherein said freezing point depressant is selected from the group consisting of polyhydric alcohols, sugars, cryo protective salts and mixtures thereof.

4. A process according to claim 3 wherein the resultant mixture has a calculated water activity value of less than about 0.95.

5. A process according to claim 4 wherein the calculated water activity of the resultant mixture is less than about 0.9.

6. A process according to claim 5 wherein the concentration of said freezing point depressant in the resultant mixture is at least 40 weight %, based on the total weight of the resultant mixture.

7. A process according to claim 5 wherein the concentration of said freezing point depressant in said anti-freeze agent is at least 50 weight %, based on the total weight of said anti-freeze agent.

8. A process according to claim 5 wherein said anti-freeze agent includes water in an amount less than about 20 weight %, based on the total weight of said anti-freeze agent.

9. A process according to claim 8 wherein
said polyhydric alcohol is selected from the group consisting of glycerol, propylene glycol, polyethylene glycol, sorbitol, mannitol and mixtures thereof,
said sugar is selected from the group consisting of invert sugar, fructose, corn syrup, hydrolyzed corn syrup, high fructose corn syrup, dextrose, sucrose, maltose, lactose, other levulose-containing carbohydrates and mixtures thereof, and
said cyroprotective salts is selected from the group consisting of glutamates, gluconates, cyclomates and mixtures thereof.

10. A process according to claim 9 wherein said anti-freeze agent includes about 80 weight % of a high fructose corn syrup, about 10 weight % glycerol, about 5 weight % monosodium glutamate and about 5 weight % water, all based on the total weight of said anti-freeze agent.

11. A process according to claim 9 wherein said anti-freeze agent includes about 40 weight % glycerol, about 40 weight % invert sugar, about 10 weight % monosodium glutamate, and about 10 weight % water, all based on the total weight of said anti-freeze agent.

12. A concentrated bacterial culture comprising live bacterial cells containing an anti-freeze agent including at least one water freezing point depressant which is water soluble, is non-injurious to the bacteria, and does not form crystals when cooled to a predetermined temperature within the range of about 5° to about −40° C., the amount of said water freezing point depressant in said anti-freeze agent being sufficient to prevent formation of ice crystals from the water present in said culture when cooled to said predetermined temperature.

13. A concentrated bacterial culture according to claim 12 wherein the bacteria selected is an organism falling within the classification Eubacteriales.

14. A concentrated bacterial culture according to claim 13 wherein the calculated water activity value is less than about 0.90.

15. A concentrated bacterial culture according to claim 14 wherein said water freezing point depressant is selected from the group consisting of glycerol, propylene glycol, polyethylene glycol, sorbitol, mannitol, invert sugar, fructose, corn syrup, hydrolyzed corn syrup, high fructose corn syrup, dextrose, maltose, lactose, other levulose-containing carbohydrates, glutamates, gluconates, cyclomates, and mixtures thereof.

16. A concentrated bacterial culture according to claim 15 wherein said anti-freeze agent includes about 80 weight % of a high fructose corn syrup, about 10 weight % glycerol, about 5 weight % monosodium glutamate and about 5 weight % water, all based on the total weight of said anti-freeze agent.

17. A concentrated bacterial culture according to claim 16 containing at least 40 weight % of said water freezing point depressant, based on the total weight of said culture.

* * * * *